United States Patent [19]

Adachi

[11] Patent Number: 5,236,823
[45] Date of Patent: Aug. 17, 1993

[54] DETECTION METHOD OF ABNORMALLY-RESPONDING LYMPHOCYTES AS WELL AS DETECTION REAGENT AND KIT THEREFOR

[75] Inventor: Masakazu Adachi, Takasaki, Japan

[73] Assignee: Japan Immuno Research Laboratories Co., Ltd., Takasaki, Japan

[21] Appl. No.: 224,712

[22] Filed: Jul. 27, 1988

[30] Foreign Application Priority Data

Jul. 31, 1987 [JP] Japan ................... 62-192338
Jul. 21, 1988 [JP] Japan ................... 63-182632

[51] Int. Cl.$^5$ ................ C12Q 1/70; C12Q 1/00; G01N 33/53; G01N 33/566; C07G 17/00; C07H 1/00; C08B 37/00; C07K 3/00
[52] U.S. Cl. .................... 435/5; 435/240.27; 435/7.2; 435/7.23; 435/7.24; 435/7.92; 436/501; 436/503; 536/123; 530/395
[58] Field of Search ............. 435/5, 7, 239, 70.21, 435/7.1, 9, 240.27, 7.2, 7.23, 7.24, 7.92; 424/89, 88; 436/501, 503, 507, 534, 540; 536/123; 530/395, 324

[56] References Cited

U.S. PATENT DOCUMENTS

| | | |
|---|---|---|
| 3,988,115 | 10/1976 | Modabber et al. |
| 4,849,510 | 7/1989 | Adachi ................... 530/395 |
| 4,904,581 | 2/1990 | Burger et al. |
| 4,917,998 | 4/1990 | Burger et al. |

FOREIGN PATENT DOCUMENTS

| | | |
|---|---|---|
| 0203552 | 3/1986 | European Pat. Off. |
| 8606413 | 11/1986 | European Pat. Off. |
| 0248534 | 9/1987 | European Pat. Off. |

OTHER PUBLICATIONS

Hakomori et al, "Novel Fucolipids Accumulating in Human Adenocarcinoma" J. Biol. Chem, 259 (1984) 4672-80.

Adachi et al, "Expression of Le$^y$ Antigen in Human Immunodificiency Virus-Infected Human T Cell Lines and in Peripheral Lymphocytes of Patients with Acquired Immune Deficiency Syndrome (AIDS) and AIDS-Related Complex".

Hakomori, "Glycosphingolipids" Scientific American vol. 254 (1986) 32-42.

Immunogenetics-vol. 17, 1983, pp. 537-541, New York, N.Y. US; K. O. Lloyd et al.

Primary Examiner—Christine M. Nucker
Assistant Examiner—D. R. Preston
Attorney, Agent, or Firm—Oblon, Spivak, McClelland, Maier & Neustadt

[57] ABSTRACT

Disclosed herein is a method for the detection of abnormally-responding lymphocytes, e.g., HIV-infected T cells by transformed cells. An antibody, which can specifically recognize a saccharide chain represented by the following formula (I):

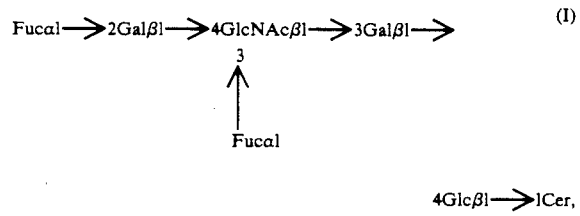

is caused to act on a sample containing lymphocytes and lymphocytes conjugated with the antibody are then detected. Reagent and kit for the above detection are also disclosed.

18 Claims, 4 Drawing Sheets

DETECTION METHOD OF ABNORMALLY-RESPONDING LYMPHOCYTES AS WELL AS DETECTION REAGENT AND KIT THEREFOR

BACKGROUND OF THE INVENTION

1. Field of the Invention

This invention relates to a method for the detection of lymphocytes which have responded abnormally to transformed cells contained in an organism, infusion or the like as well as detection reagent and detection kit useful for the method.

2. Description of the Related Art

It has been known that a serious disease is induced when intravital cells are transformed by a certain cause. For example, histocytic cells transformed by oncogenes become cancer cells and develop a cancer while $T_4$ cells transformed by an HIV virus may cause acquired immune deficiency syndrome (AIDS). In addition, hepatitis is said to be attributed to transformation of liver cells by a virus.

It is hence extremely important for the detection of the above-described diseases and the judgement of the degrees of their progress to determine the existence of transformed cells in an organism and their population.

However, the diagnosis of a disease developed by the existence of these transformed cells have heretofore been effected by detecting biochemically, hematologically or immunologically a specific change caused by the disease. These diagnoses are therefore accompanied by drawbacks that they cannot be performed with ease in an early stage of a disease in many instances and they have difficulties in determining the degree of its progress. They involve a further drawback that with respect to each disease, a reagent suited for the diagnosis of the disease must be provided.

SUMMARY OF THE INVENTION

The present inventors have carried out an extensive investigation with a view toward developing a method for detecting and diagnosing, in an early stage, cancers and various diseases caused due to infection with viruses. It has now been found that there are certain specific common characteristics on lymphocytes which have responded abnormally in the presence of transformed cells.

Namely, the investigation of the present inventors has revealed that one of saccharide chains expressed in cancer cells is expressed on T cells infected with HIV and the saccharide chain is also expressed on lymphocytes responded abnormally to these transformed cells. It has also been found that the expression of the saccharide chain on the abnormally-responding lymphocytes is stronger than that on the transformed cells and detection of the saccharide chain on the lymphocytes permits easy judgement of the development of the abnormal response by the lymphocytes to the transformed cells.

Accordingly, this invention provides a method for the detection of abnormally-responding lymphocytes, e.g., HIV-infected T cells by transformed cells, which comprises causing an antibody, which can specifically recognize a saccharide chain represented by the following formula (I):

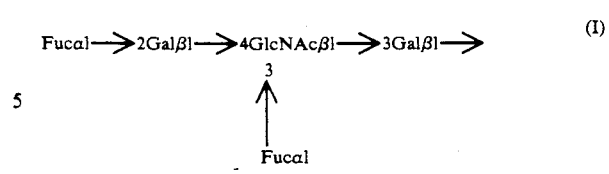

to act on a sample containing lymphocytes and then detecting lymphocytes conjugated with the antibody, and also a reagent and a kit useful for the practice of the above method.

Since any abnormal response of lymphocytes to transformed cells can be directly detected by the present invention, this invention can conduct not only the diagnoses of various diseases but also the direct determination of the degrees of progress of such diseases. The present invention does not detect transformed cells themselves but does detect lymphocytes responded abnormally to them. Accordingly, body fluids such as blood can be used and the testing has been facilitated.

DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
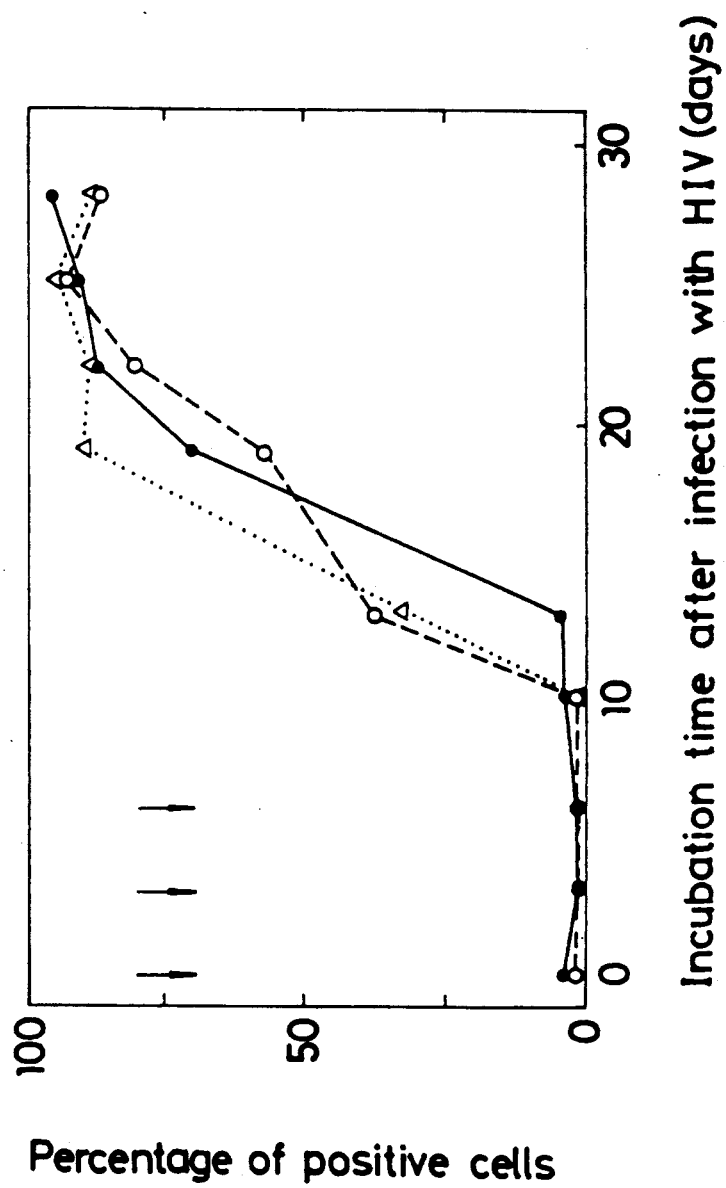
FIG. 1 illustrates the relationship between incubation time and percent positive conversion for HIV-infected T-cells.

The saccharide chain (I), which the antibody useful in the practice of this invention can recognize, has already been known as "Le$^y$ antigen" (Hakomori, S., Nudelman, E., Levery, S.B., and Kannagi, R.: J. Biol. Chem., 259, 4672–4680, 1984). It is hence possible to use, as an antibody useful in the practice of this invention, a monoclonal antibody produced, for example, by immunizing an animal with Le$^y$ antigen in a manner known per se in the art, obtaining hybridomas from antibody-producing cells of the animal by a cell fusion technique and then culturing the hybridomas. The antibody useful in the practice of this invention may be used as a crude antibody solution, namely, in the form of a culture supernatant of the anti-Le$^y$-producing hybridomas or a mouse ascitic fluid without any further treatment or processing. It may also be used after purification by ammonium sulfate fractionation, ion-exchange chromatography, or affinity chromatography on a protein A or antigen column.

As one example of antibodies available readily, may be mentioned the antibody already known as "BM-1" (Abe, K., McKibbin, J.M., and Hakomori, S.: J. Biol. Chem., 258, 11793-11797, 1983).

As samples containing lymphocytes, blood, lymph, ascitic fluid, amniotic fluid, cerebrospinal fluid and the like may be used by way of example. When blood is used, it is preferable to collect 0.1-10 ml of blood and generally, to use it as serum, plasma or lymph.

In the method of the present invention, the above-mentioned antibody-conjugated lymphocytes can be detected by a known method. This detection may be performed preferably by radioimmunoassay (RIA), enzyme immunoassay (EIA) or fluoroscent antibody technique (FAT), which is a usual immunological assay and makes use of the competitive method. Operational procedures of these techniques may be carried out in a usual manner. More specifically, T cells are isolated from a sample by a method known per se in the art. A slide glass is coated with the T cells and the antibody useful in the practice of this invention is added dropwise onto the thus-coated T cells. After washing the T-cells, they are stained with a secondary antibody by fluoroscent antibody technique or enzyme immunoassay.

As a detection method of a virus or the like which is present in serum or plasma and may transform vital cells, cultured cell line T cells (H-9, TALL-1) are exposed to a serum or plasma to be tested so as to infect the cells by a virus or the like contained in the serum or plasma, and the virus or the like present in the serum or plasma can then be detected as described above.

Labelling of the antibody, which is useful in the practice of this invention, with an enzyme as a marker may be carried out by the method described in Tanpakushitsu·Kakusan·Koso (Proteins·Nucleric Acids·Enzymes) 20(11), 1007-1013 (1975). Labelling of the antibody with a fluorescent marker may be conducted following the method described in Kiso Seikagaku Jikkenho (Basic Biochemical Experimental Procedures) Vol. 6 (Biochemical Assays), page 167. Any antibody may be used here so long as it has binding ability for the aforementioned antibody.

For example, the secondary antibody may be obtained by immunizing an animal other than human being, such as a rabbit, goat, mouse or the like, with an antibody employed as a primary antibody in a kit and then collecting same from serum or ascitic fluid or by purchasing an antibody, which can specifically bind the aforementioned antibody, for each isotype. The enzyme-labelled or fluorescence-labelled secondary antibody may be prepared in the above-described manner or a commercial product may be purchased. A suitable enzyme substrate solution may be chosen in accordance with the kind of the enzyme carried on the antibody. That is, a 3',3'-diaminobenzidine solution, 9-amino-9-ethylcarbamizole solution or the like may be used where the enzyme is horse raddish peroxidase, whereas a p-toluidine 5-bromo-4-chloro-3-indolylphosphate solution or the like may be employed where the enzyme is an alkali phosphatase.

A suitable staining agent may be chosen depending on the enzyme. 5-aminosalicylic acid, o-phenylenediamine or the like may be used where the enzyme is horse raddish peroxidase, while p-nitrophenyl phosphate or the like may be employed where the enzyme is an alkali phosphatase.

In a direct method, an antibody itself is fluoroscence- or enzyme-labelled and the thus-labelled antibody is used. Although the direct method therefore requires fewer staining steps compared with an indirect method making use of a secondary antibody, it is accompanied by a drawback that the background is high. The fluorescent antibody technique making use of a fluoroscent marker requires fewer steps and is thus simple and convenient.

The method of this invention can be easily and conveniently practiced by using a reagent which contains an antibody capable of specifically recognizing the saccharide chain of the formula (I). It may be practiced more easily and conveniently by additionally using (1) a kit for the direct fluorescent antibody technique, said kit containing a fluorescence-labelled antibody useful in the practice of this invention, (2) a kit for the indirect fluorescent antibody technique, said kit containing the antibody useful in the practice of this invention and a secondary antibody carrying thereon a fluorescent marker capable of binding the antibody, (3) a kit for the direct enzyme antibody technique, said kit containing an enzyme-labelled antibody useful in the practice of this invention, (4) a kit for the indirect enzyme antibody technique, said kit containing an antibody useful in the practice of this invention and a secondary antibody carrying thereon an enzymatic marker capable of binding the antibody, or the like.

The kit is supposed to contain an antibody useful in the practice of this invention and a secondary antibody. The kit may also contain, for example, a stabilizer such as glycerol or bovine serum protein and/or a preservative. The antibody reagent may be lyophilized and the kit may contain a water-soluble or water-miscible solvent. The antibody reagent may also be added with a buffer for maintaining the thus-reconstituted reagent at a constant pH and/or a preservative and/or a stabilizer for preventing deterioration of a sample. Although the buffer is not an essential component of the kit reagent, it is preferable to use a buffer capable of controlling the pH of the kit reagent within a range of from about 5.0 to about 9.0 upon practise of the assay of this invention. Although the reconstituting agent may preferably be that containing water, a portion or the whole portion of the water may be replaced by a solvent miscible with water. As illustrative examples of the water-miscible solvent, may be mentioned glycerin, alcohols, glycol ethers, etc., all of which are well known in the art.

Lymphocytes which have abnormally responded and are detectable by the method of the present invention reflect the existence of transformed cells. The term "transformed cells" as used herein means those occurred due to infection of cells with a virus, canceration of cells and the like and causing, for example, various cancers, AIDS, hepatitis, certain mental diseases, auto-immune diseases, etc.

It is however evident from subsequent examples that lymphocytes detectable in accordance with this invention are not transformed cells themselves. Namely, It has been demonstrated that lymphocytes, which may be infected with HIV, are not $T_8$ cells but $T_4$ cells but those reactive most strongly to $Le^y$ antigen are $T_8$ cells which are not infected with HIV.

The present invention will hereinafter be described in further detail by the following examples.

EXAMPLE 1

Peripheral blood samples drawn respectively from healthy subjects and patients of various diseases caused by the existence of transformed cells or probably attributed to their existence were subjected to two-color flow cytometry to check for the existence of Le$^y$ antigens expressed on T-cells. The tested subjects consisted of 27 healthy subjects, 10 cancer patients, 80 HIV patients, 31 schizopherenia patients, 13 hepatitis patients, 1 Guillain-Barre syndrome patient, and 1 Sezary syndrome patient. Results are summarized in Table 1.

For the two-color flow cytometry, 10 ml of heparinized blood was drawn from each subject's vein, added to 1 ml of "KAC-2" (trade name; 5% silica suspension; product of Japan Immunoresearch Laboratories), and, to eliminate phagocytotic cells, incubated for one hour at 37° C., after which the blood was subjected to FICOLL-HYPAQUE gradient centrifugation to yield a mononuclear fraction. Next, the lymphocytes ($5-10 \times 10^5$ cells/100 µl) were mixed with 100 µl of BM-1 antibody at a concentration of 5 µg/ml, incubated for one hour, and washed once in a phosphate buffer saline solution (PBS). The mixture was then added with 100 µl of FITC conjugated anti-mouse IgM (product of Tago Inc.) at a concentration of 15 µg/ml, incubated for 30 minutes, and again washed once with PBS. Subsequently 10 µl of T-cell markers CD3 (Pan-T marker), CD4 (helper/inducer T marker), or CD8 (suppressor/killer T marker)—all from Becton Dickinson and Co.—was added, and the resultant mixture was incubated for 30 minutes, washed once with PBS. After the washing, the resulting cells were added with 1 ml of 1.5% formalin in PBS, fixed for 15 minutes in ice water, and then washed once with PBS. Finally, 300 µl of PBS was added to prepare a cell suspension and then subjected to an analysis. To detect the FITC-conjugated BM-1 antibody, the suspension was analyzed at an excitation wavelength of 488 nm and a fluorescence wavelength of 520 nm. Measurement of T-cell markers directly marked with phycoerythin were, however, conducted by measuring the fluorescence strength at an excitation wavelength of 488 nm and a fluorescence wavelength of 580 nm.

[Results]

| Subjects | n | Le$^y$ antiboty level in T-3 cells | in T-4 cells | in T-8 cells |
|---|---|---|---|---|
| Healthy | 27 | 9.3 ± 0.77 | 10.0 ± 0.66 | 11.4 ± 1.25 |
| Cancer | | | | |
| P.S.* 3, 4 | 5 | 14.7 ± 0.57 | 14.9 ± 1.42 | 22.6 ± 1.7 |
| P.S.* 0, 1, 2 | 5 | 16.2 ± 5.09 | 17.7 ± 4.54 | 17.1 ± 5.11 |
| HIV | | | | |
| CDC** IV | 31 | 15.5 ± 2.18 | 24.8 ± 3.22 | 22.1 ± 2.44 |
| CDC** II, III | 49 | 6.9 ± 0.74 | 7.8 ± 0.83 | 14.8 ± 1.56 |
| Schizophrenia | | | | |
| Active phase | 26 | 19.1 ± 1.97 | 20.3 ± 2.03 | 24.0 ± 2.11 |
| Inactive phase | 5 | 12.6 ± 2.09 | 13.6 ± 2.54 | 18.5 ± 2.41 |
| Hepatitis | | | | |
| Acute | 4 | 15.6 ± 4.08 | 92 ± 2.36 | 25.0 ± 3.75 |
| Chronic | 9 | 10.1 ± 1.24 | 10.7 ± 1.32 | 7.7 ± 1.32 |
| Guillain-Bare syndrome | 1 | 18.6 | 19.6 | 46.6 |
| Sezary syndrome | 1 | 11.6 | 17.5 | 27.1 |

P.S. Patient's status

| 0 | Patient is entirely without symptoms, can take part in social activities, and is able to move without retriction as before the onset of the illness. |
|---|---|
| 1 | Has slight symptoms which limit his ability to do physical work, but can walk and perform light labor such as house or office work. |
| 2 | Sometimes requires assistance in walking or in performing minor tasks. Cannot perform light work, but is out of bed at least half of the day. |
| 3 | Frequently requires assistance in performing minor tasks, and spends more than half of the day in bed. |
| 4 | Normally requires assistance even in minor tasks, and spends the entire day in bed. |
| I | Tests positive to anti-HIV antibodies, and has transient symptoms peculiar to the early stage of HIV infection. |
| II | Has no symptoms of infection, but tests positive for anti-HIV antibodies. |
| III | Has continous, body-wide enlargement of lymphnodes, i.e., has lymphnode swelling of at least 1 cm for at least 3 months in at least two areas outside the groin, but has no other symptoms. |
| IV | Subgroup A — Has continous, body-wide symptoms (fever, weight loss, diarrhea, etc.). |
| | Subgroup B — Has neurotic symptoms (e.g., dementia, myelopathy, peripheral neuropathy). |
| | Subgroup C — Has cellular immune deficiency caused by HIV infection. |
| | Subgroup D — Has secondary malignant tumors caused by HIV infection. |
| | Subgroup E — Class IV patients who do not fall under categories A-D. |

With combinations of BM-1 and various T-cell markers, tests were conducted on the 10 advanced cancer patients whose cancers were clearly observable on X-ray or CT scan pictures (5 patients at P.S.'s 3 and 4; 5 patients at P.S.'s 0, 1 and 2). As a result, expression of Le$^y$ was observed on T-cell subsets, CD4 (helper/inducer T-cells) and CD8 (suppressor/killer T-cells). In particular, strong expression of Le$^y$ was observed on CD8 cells of patients with high P.S. numbers.

Strong expression of Le$^y$ was also observed on CDC IV patients (those with apparent clinical symptoms), rather than in CDC III patients (those with lasting, body-wide lymphnode enlargement) or CDC II patients considered to be HIV carriers.

With the schizopherenia patients, analysis of peripheral lymphocytes drawn from the patients both in active and inactive phases revealed an unusual staining pattern in the lymphocytes of the active phase patients, and showed a high level of Le$^y$ expression on T-cells. Although the patients in the inactive phase had a similar unusual pattern in their peripheral lymphocytes, their levels of Le$^y$ expression were not significantly different from those of healthy subjects.

The lymphocytes of the single Guillain-Barre syndrome patient showed an usual staining pattern, and a high level of Le$^y$ expression was observed on T-cells. The Sezary syndrome patient, who was probably infected with an unknown virus and whose helper T-cells were reported hyperactive, had been classified as carrying a type of leukemia. That patient showed an unusual Le$^y$ staining pattern in marker CD4-positive cells of helper T-cells.

From these results, it is indicated that Le$^y$ antibody is expressed by lymphocytes which respond abnormally due to the presence of virus-infected or cancerous cells (transformed cells), and that the detection of the antibody makes it possible both to predict the onset of symptoms and to diagnose already apparent symptoms for patients with a variety of illness.

EXAMPLE 2

Expression of Antibodies over Time by HIV-Infected Cells

TALL-1 cells were cultured in RPMI-1640 supplemented with 10% heat-inactivated fetal calf serum containing 50 μg/ml of gentamycin. HIV having reverse transcriptase activity of 58000 cpm/ml containing 1 μg/ml of "Polybrene" (trade mark; product of Sigma Chemical Company, St. Louis, Mo.) was added to a $3 \times 10^5$/ml suspension of the TALL-1 cells on the 1st, 3rd, and 6th days as shown by arrows in FIG. 1, and HIV antigens expressed on the cell surfaces were analyzed.

The analysis was carried out by cytofluorometry, using anti-p24 monoclonal antibodies, blood serum from AIDS patients, and BM-1 antibodies, whereby the ratio of positive cells was determined.

In FIG. 1, ●——● stands for the reactivity with BM-1 antibody, ○---○ for the reactivity with the patient's blood serum, and △...△ for the reactivity with anti-p24.

As a result of the above experiment, it has become evident that from the 18th day after infection with HIV, TALL-1 cells begin to change to positive cells which react strongly with BM-1 antibody.

EXAMPLE 3

Cytofluorometric Analysis of Membrane Antigen $5 \times 10^5$ cell portions of HIV-infected or uninfected H-9 cells or TALL-1 cells were mixed respectively with 100 μl of various refined antibodies, and after incubation at 4° C. for 60 minutes, were separately washed twice with RPMI-1640 medium. The resultant solutions were each added with 100 μl of 35-times diluted FITC-conjugated goat F(ab)₂ fragment directed to anti-mouse IgM or IgG (Tago Inc.; Code No. 4352). After incubation at 4° C. for 30 minutes, the cells were washed twice with RPMI medium and fixed with 1.5% formalin-PBS. Purified mouse IgM (Coulter Corporation) was used as a primary antibody for a control. Cytofluorometry was performed using an EPICS-C (Coulter Electronics), and the results are shown in FIG. 2.

Figure 2:
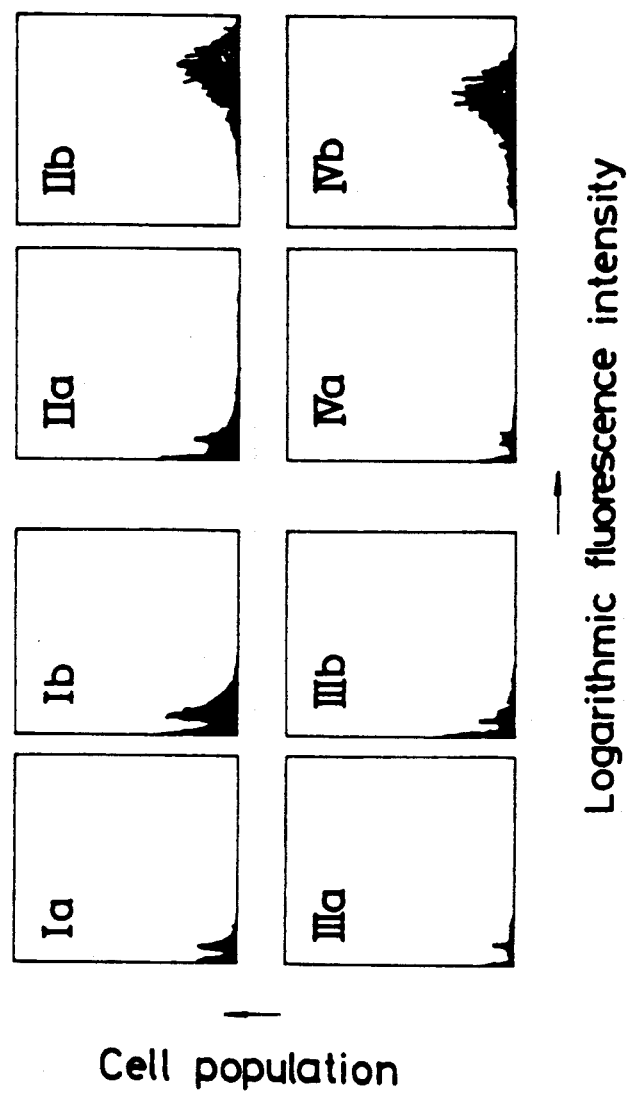
FIG. 2 illustrates results of cytofluorometric analyses conducted respectively on various refined antibodies to detect HIV-infected and uninfected T-cells.

The graphs in FIG. 2 are assigned as follows:
Ia: HIV-uninfected H-9 cells treated with mouse IgM.
Ib: HIV-infected H-9 cells treated with mouse IgM.
IIa: HIV-uninfected H-9 cells treated with BM-1 monoclonal antibody.
IIb: HIV-infected H-9 cells treated with BM-1 monoclonal antibody.
IIIa: HIV-uninfected TALL-1 cells treated with mouse IgM.
IIIb: HIV-infected TALL-1 cells treated with mouse IgM.
IVa: HIV-uninfected TALL-1 cells treated with monoclonal antibody BM-1.
IVb: HIV-infected TALL-1 cells treated with monoclonal antibody BM-1.

As shown in FIG. 2, Groups IIb and IVb both expressed strong fluorescence. Namely, both the HIV-infected H-9 and TALL-1 cells, after treatment with BM-1, showed an increase in fluorescence intensity.

EXAMPLE 4

Figure 3:
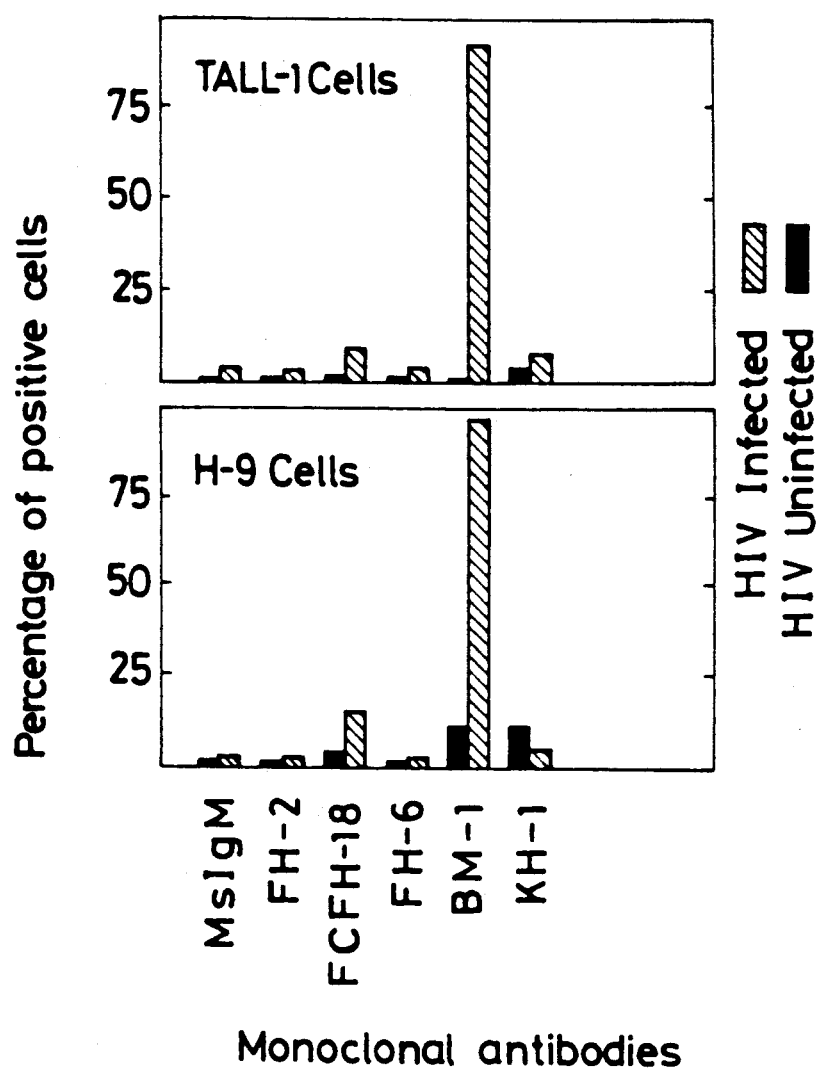
FIG. 3 depicts the reactivity between T-cells and various antibodies.

For each type of cells, the difference between their reactivity with each antibody both before and after infection with HIV was determined. Results are shown in FIG. 3. As illustrated there, it is understood that the established cell lines, T-cells (H-9, TALL-1), react strongly with BM-1 antibody only after infection with HIV.

The antibodies used in this experiment were prepared by the procedures described respectively in the following articles:

FH-2: Fukushi, Y., et al., J. Biol. Chem., 259, 4681–4685, 1984.
ACFH-18: Fukushi, Y., et al., J. Biol. Chem., 259, 4681–4685, 1984.
FH-6: Fukushi, Y., et al., J. Biol. Chem., 259, 10501–10517, 1984.
KH-1: Kaizu, T., et al., J. Biol. Chem., 261, 11254–11258, 1986.

EXAMPLE 5

Separation and Immunofluorescent Staining of Human Peripheral Lymphocytes

Heparinized blood samples (10 ml) drawn respectively from AIDS and ARC patients' veins were each mixed with 2 ml of "KAC-2" (trade name; 5% silica suspension; product of Japan Immunoresearch Laboratories) and after elimination of phagocytotic cells, maintained at 37° C. for one hour. The KAC-2 treated blood samples were then subjected separately to FICOLL-HYPAQUE gradient centrifugation to obtain mononuclear cell fractions. Alliquots of the lymphocytes were stained by immunofluorescence with various antibodies. Results are depicted in FIGS. 4(A) through 4(D).

Figure 4B:
FIG. 4(B) is a fluorescent micrograph of T-cells of an AIDS patient.
Figure 4D:
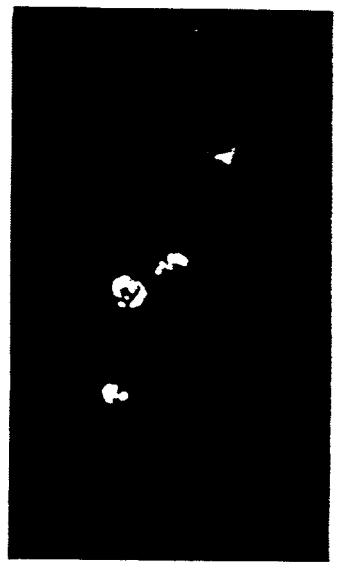
FIG. 4(D) is a fluorescent micrograph of T-cells of an ARC patient.
Figure 4A:
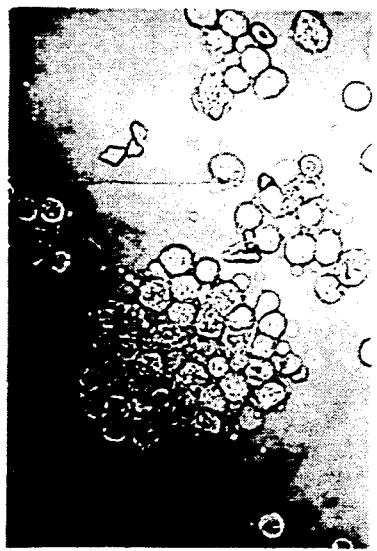
FIG. 4(A) is an optical micrograph of T-cells of an AIDS patient.
Figure 4C:
FIG. 4(C) is an optical micrograph of T-cells of an ARC patient.

FIG. 4(A) is an optical micrograph of T-cells of an AIDS patient, and FIG. 4(B) a fluorescent micrograph of same. Further, FIG. 4(C) is an optical micrograph of T-cells of an ARC patient, and FIG. 4(D) a fluorescent micrograph of same.

As is shown in FIG. 4(B), the lymphocytes of the AIDS patient reacted strongly with BM-1 antibody. However, the ARC patient's lymphocytes showed much weaker fluorescence staining than those of the AIDS patient as shown in FIG. 4(D).

I claim:

1. A method of testing for the presence of lymphocytes expressing a saccharide chain of formula I, comprising the steps of:

a) contacting lymphoccytes which express a saccharide chain of formula I

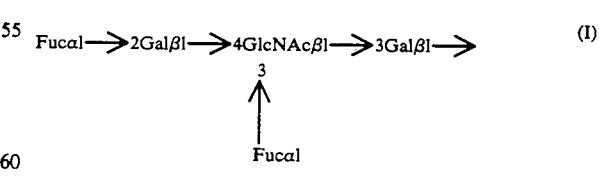

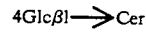

with labeled conjugating antibodies which recognize said saccharide chain to form an antibody-lymphocyte conjugate, and b) directly or indirectly detecting the presence of said label.

2. The method of claim 1, wherein said lymphocytes are T₄ lymphocytes.

3. The method of claim 1, wherein said conjugating antibodies are BM-1 antibodies.

4. The method of claim 1, wherein said lymphocytes are present in blood serum, blood plasma, lymph, ascitic fluid, amniotic fluid or cerebrospinal fluid.

5. The method of claim 1, wherein said label is a fluorescent marker and said detecting step comprises directly detecting said fluorescent marker.

6. the method of claim 1, wherein said label is a fluorescent marker and said detecting step comprises indirectly detecting said fluorescent marker by contacting said conjugate with a fluorescent marker labeled antibody which recognizes said conjugating antibody.

7. The method of claim 1, wherein said label is an enzyme label and said detecting step comprises directly detecting said enzyme label.

8. The method of claim 1, wherein said label is an enzyme label and said detecting step comprises indirectly detecting said enzyme label by contacting said conjugate with an enzyme labeled antibody which recognizes said conjugating antibody.

9. The method of claim 1, wherein said label is a radioactive label and said detecting step comprises directly detecting said radioactive label.

10. The method of claim 1, wherein said lymphocytes are T₈ lymphocytes.

11. A method for diagnosing cancer, a viral infection or disease states associated with cancer or a viral infection in a patient, comprising the steps of:

a) contacting lymphocytes which express a saccharide chain of formula I

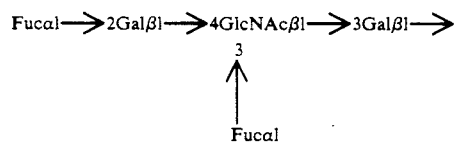

(I)

with labeled conjugating antibodies which recognize said saccharide chain to form an antibody-lymphocyte conjugate, b) directly or indirectly detecting the presence of said label, and c) correlating the amount of said detected label to the occurrence of cancer, viral infection or a disease state associated with cancer or viral infection.

12. The method of claim 11, wherein said patient is a cancer patient.

13. The method of claim 11, wherein said viral infection is hepatitis.

14. The method of claim 11, wherein said viral infection is HIV infection.

15. The method of claim 11, wherein said lymphocytes are T₄ lymphocytes.

16. The method of claim 11, wherein said lymphocytes are T₈ lymphocytes.

17. The method of claim 11, wherein said conjugating antibodies are BM-1 antibodies.

18. A kit for the detection of lymphocytes, comprising a mixture of:

a) antibodies which recognize a saccharide chain of formula I, $$\text{Fuc}\alpha1 \rightarrow 2\text{Gal}\beta1 \rightarrow 4\text{GlcNAc}\beta1 \rightarrow 3\text{Gal}\beta1 \rightarrow \underset{\underset{\text{Fuc}\alpha1}{\uparrow}}{3} \quad \text{(I)}$$

$$4\text{Glc}\beta1 \rightarrow \text{Cer}$$

b) a silica suspension, and c) a lymphocyte fixative, in at least one container.

* * * * *